United States Patent
Campbell, Jr. et al.

(10) Patent No.: US 6,806,327 B2
(45) Date of Patent: Oct. 19, 2004

(54) SUBSTITUTED POLYCYCLIC, FUSED RING COMPOUNDS, METAL COMPLEXES AND POLYMERIZATION PROCESS

(75) Inventors: Richard E. Campbell, Jr., Midland, MI (US); Jerzy Klosin, Midland, MI (US); Ravi B. Shankar, Midland, MI (US); Francis J. Timmers, Midland, MI (US); Robert K. Rosen, Houston, TX (US); Shaoguang Feng, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/124,269

(22) Filed: Apr. 16, 2002

(65) Prior Publication Data

US 2002/0151662 A1 Oct. 17, 2002

Related U.S. Application Data

(63) Continuation-in-part of application No. 09/879,463, filed on Jun. 12, 2001, now Pat. No. 6,613,921.
(60) Provisional application No. 60/215,456, filed on Jun. 30, 2000.

(51) Int. Cl.[7] ............................ C08F 4/44; C08F 4/642; C08F 4/643; C07F 17/00; C07C 13/68
(52) U.S. Cl. ...................... 526/127; 526/134; 526/160; 526/161; 526/170; 526/172; 502/103; 502/117; 502/152; 502/155; 556/7; 556/11; 556/43; 556/52; 556/53; 556/58; 556/136; 556/140; 585/21; 585/26
(58) Field of Search ................................ 556/7, 11, 43, 556/52, 53, 58, 140, 136, 12, 20, 23, 46; 526/170, 172, 127, 134, 160, 161; 502/103, 117, 152, 155; 585/21, 26

(56) References Cited

U.S. PATENT DOCUMENTS

| 5,321,106 | A | 6/1994 | LaPointe |
| 5,374,696 | A | 12/1994 | Rosen et al. |
| 5,470,993 | A | 11/1995 | Devore et al. |
| 5,486,632 | A | 1/1996 | Devore et al. |
| 5,489,659 | A | 2/1996 | Sugano et al. |
| 5,510,502 | A | 4/1996 | Sugano et al. |
| 5,541,349 | A | 7/1996 | Wilson et al. |
| 5,561,093 | A | 10/1996 | Fujita et al. |
| 5,594,081 | A | 1/1997 | Uchino et al. |
| 5,703,187 | A | 12/1997 | Timmers |
| 5,721,185 | A | 2/1998 | LaPointe et al. |
| 6,340,652 | B1 * | 1/2002 | Sugano et al. .............. 502/118 |

FOREIGN PATENT DOCUMENTS

| EP | 697418 B1 | 2/1996 |
| WO | WO 97/15583 | 5/1997 |
| WO | WO 97/19463 | 5/1997 |
| WO | WO 99/02540 | 1/1999 |
| WO | WO 99/14221 | 3/1999 |

OTHER PUBLICATIONS

Ried et al., Liebigs Ann. Chem. 1974, pp. 1239–1247.*

* cited by examiner

*Primary Examiner*—Roberto Rabago

(57) ABSTRACT

Metal complexes comprising a polycyclic, fused ring ligand or inertly substituted derivative thereof comprising at least: (1) a cyclopentadienyl ring, (2) a 7 membered polyatomic ring, and (3) one or more aromatic ring systems, with the proviso that said 7 membered ring (2), is fused to both the cyclopentadienyl ring (1), and said one or more aromatic ring systems (3), and substituted in at least one ring position with a substituent group resulting in $sp^2$ hybridization on the ring atom bonded thereto; polymerization catalysts; and olefin polymerization processes using the same are disclosed.

9 Claims, No Drawings

SUBSTITUTED POLYCYCLIC, FUSED RING COMPOUNDS, METAL COMPLEXES AND POLYMERIZATION PROCESS

CROSS REFERENCE STATEMENT

This application is a continuation-in-part of U.S. Ser. No. 09/879,463, filed Jun. 12, 2001, now U.S. Pat. No. 6,613,921 and claims the benefit of U.S. Provisional Application No. 60/215,456, filed Jun. 30, 2000.

BACKGROUND OF THE INVENTION

This invention relates to a class of polycyclic, fused ring compounds, metal complexes formed therefrom, and to polymerization catalysts derived from such complexes that are particularly suitable for use in a polymerization process for preparing homopolymers and copolymers of olefins or diolefins, including copolymers comprising two or more olefins or diolefins such as copolymers comprising a monovinyl aromatic monomer and ethylene.

Constrained geometry metal complexes and methods for their preparation are disclosed in U.S. Pat. No. 5,703,187. This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. Pat. Nos. 5,321,106, 5,721,185, 5,374,696, 5,470,993, 5,541,349, and 5,486,632, as well as WO97/15583, and WO97/19463.

Certain highly active, polyaromatic, metal complexes, especially derivatives of cyclopentaphenanthrenyl ligand groups are disclosed in U.S. Ser. No. 09/122,958, filed Jul. 27, 1998, now U.S. Pat. No. 6,150,297 (WO99/14221, published Mar. 25, 1999). Metallocenes containing four fused rings arranged on a central 5-membered carbon ring are disclosed in WO99/02540.

Despite the advance in the art obtained by the foregoing metal complexes, catalysts possessing improved catalytic performance are still desired by the industry. Accordingly, it would be desirable if there were provided metal complexes having improved catalytic properties to the foregoing known compounds.

SUMMARY OF THE INVENTION

According to the present invention there is provided a polycyclic, fused ring compound corresponding to the formula: $(Cp^*)_p$—$M^*$ (I) or $CpM(Z)_z(X)_x(L)_1(X')_{x'}$(II), where $Cp^*$ is a polycyclic, fused ring ligand or inertly substituted derivative thereof comprising at least: (1) a cyclopentadienyl ring, (2) a 7 membered polyatomic ring, and (3) one or more aromatic ring systems, with the proviso that said 7 membered ring (2), is fused to both the cyclopentadienyl ring (1), and said one or more aromatic ring systems (3), and substituted in at least one ring position with a substituent group resulting in $sp^2$ hybridization on the ring atom bonded thereto, said $Cp^*$ having up to 60 atoms other than hydrogen;

p is 1 or 2;

when p is 1, $M^*$ is hydrogen, an alkali metal or an alkaline earth metal halide, and, when p is 2, $M^*$ is an alkaline earth metal; said $M^*$ being bound to at least one of the non-fused, ring-carbons of the cyclopentadienyl ring, (1);

Cp is the aromatic ligand group derived from $Cp^*$ by removal of $M^*$;

M is a metal selected from Groups 3–10 or the Lanthanide series of the Periodic Table of the Elements;

Z is either:

a) a cyclic ligand group containing delocalized $\pi$-electrons, including a second or third, fused, polycyclic ligand, Cp, said Z being bonded to M by means of delocalized $\pi$-electrons and optionally also covalently bonded to Cp through a divalent bridging group, Z', or b) a divalent moiety of the formula —Z'Y—, wherein, Z' is $SiR^6_2$, $CR^6_2$, $SiR^6_2SiR^6_2$, $CR^6_2CR^6_2$, $CR^6$=$CR^6$, $CR^6_2SiR^6_2$, $BR^6$, $BR^6L''$, or $GeR^6_2$;

Y is —O—, —S—, —$NR^5$—, —$PR^5$—; —$NR^5_2$, or —$PR^5_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;

L'' is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;

z is 0, 1 or 2;

x is 0, 1, 2, or 3;

t is a number from 0 to 2, and x' is 0 or 1.

The above compounds may exist as isolated crystals, as a mixture with other compounds, in the form of a solvated adduct, dissolved in a solvent, especially an organic liquid solvent, in the form of a dimer, or as a chelated derivative, especially wherein the chelating agent is an organic material such as ethylenediaminetetraacetic acid (EDTA).

Also, according to the present invention, there is provided a catalyst for olefin polymerization comprising:

A. i) a metal compound of formula (II), and
   ii) an activating cocatalyst,
the molar ratio of i) to ii) being from 1:10,000 to 100:1, or
B. the reaction product formed by converting a metal compound of formula (II) to an active catalyst by use of an activating technique.

Further according to the present invention there is provided a process for the polymerization of olefins comprising contacting one or more $C_{2-20}$ olefins, including cyclic olefins, under polymerization conditions with a catalyst comprising:

A. i) a metal compound of formula (II), and
   ii) an activating cocatalyst,
the molar ratio of i) to ii) being from 1:10,000 to 100:1, or
B. the reaction product formed by converting a metal compound of formula (II) to an active catalyst by use of an activating technique.

The present catalysts and polymerization processes are especially efficient for production of olefin homopolymers, copolymers of two or more olefins, in particular, copolymers of ethylene and a vinylaromatic monomer, such as styrene, and interpolymers of three or more polymerizable monomers over a wide range of polymerization conditions, and especially at elevated temperatures. They are especially useful for the formation of ethylene homopolymers, copolymers of ethylene and one or more higher α-olefins (that is, olefins having 3 or more carbon atoms), copolymers of ethylene, propylene and a diene (EPDM copolymers), copolymers of ethylene and vinylaromatic monomers such as styrene (ES polymers), copolymers of ethylene, styrene, and a diene (ESDM polymers), and copolymers of ethylene, propylene and styrene (EPS polymers). Examples of suitable diene monomers include ethylidenenorbornene, 1,4-hexadiene or similar conjugated or nonconjugated dienes. Surprisingly, the metal complexes of formula (II) demonstrate equivalent or improved catalytic properties compared to metal complexes containing polycyclic, fully aromatic, hydrocarbon ligands, and they and their degradation products are more biologically inert compared to compounds containing fused, polycyclic, fully aromatic hydrocarbon ligands.

The catalysts of this invention may also be supported on a solid material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

The compounds of formula (I) are useful in the formation of the compounds of formula (II) as well as in the preparation of other metal complexes. In addition to their use as polymerization catalysts, compounds according to the present invention may be used for hydroformulation, hydrogenation or oligomerization processes.

DETAILED DESCRIPTION OF THE INVENTION

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups. The contents of any patent, patent application or publication referenced herein is hereby incorporated by reference in its entirety herein, especially with respect to its disclosure of organometallic structures, synthetic techniques and general knowledge in the art. As used herein the term "aromatic" refers to a polyatomic, cyclic, ring system containing (4δ+2) π-electrons, wherein δ is an integer greater than or equal to 1. The term "fused" as used herein with respect to two polyatomic, cyclic rings means that such rings have two adjacent atoms thereof common to both rings. The term "fused" as used herein with respect to a ring system containing more than two polyatomic, cyclic rings, means that at least two rings thereof are fused together.

In the foregoing metal complexes of formula (I), although M* is depicted as being bonded to only one carbon atom of Cp, it is to be understood that when M* is not hydrogen, more than one such carbon atom of Cp may share such bond to M*. The metal complexes of formula (II) include complexes containing 1, 2, or 3 Cp groups, including those wherein two such Cp or other Z groups are bound together by a bridging group. Such complexes are analogous structurally to metallocenes containing 1, 2 or 3 cyclopentadienyl groups, or inertly substituted derivatives thereof. Both symmetrical or unsymmetrical compounds are included, that is, compounds containing two dissimilar π-bonded groups, including those containing two Cp groups or a Cp and a π-bonded Z group that is not a Cp group.

Desirably, in the compounds of the invention, the ring (2) is a 7-membered, non-aromatic ring. Even more desirably, the metal compounds of formula (II) contain a cyclopentadienyl ring and two aromatic ring systems fused to the 7-membered ring at positions adjacent to the cyclopentadienyl ring thereby leaving one remaining ring position on the 7-membered ring, the cyclopentadienyl ring (1) and the aromatic rings (3) are not fused together, and the sp² hybridized element is located at the remaining 7-membered ring position lying between the two aromatic ring systems (3).

Preferred compounds of formula (I) of the invention are those corresponding to the formula:

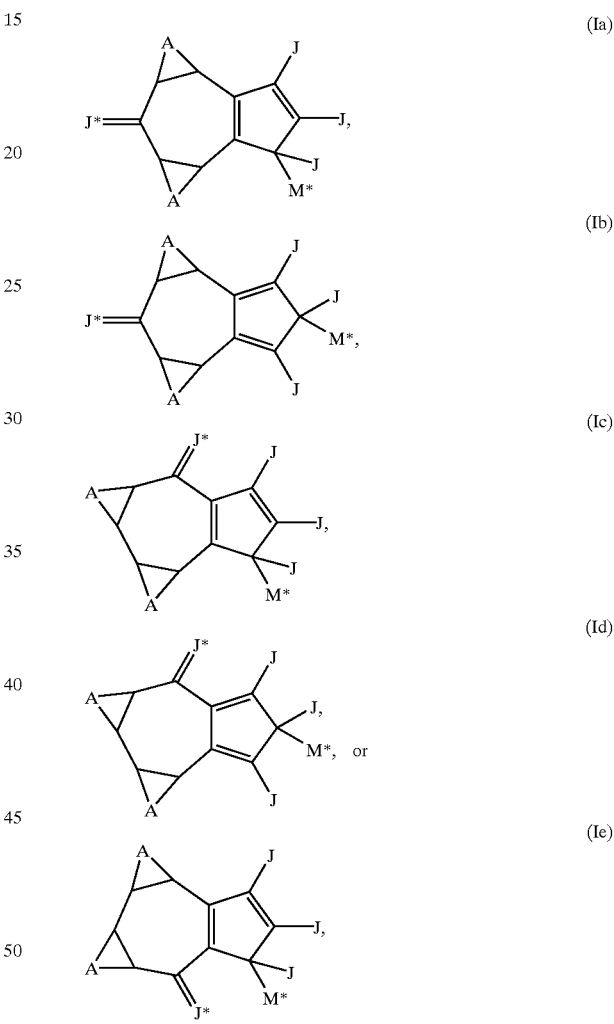

structural isomers thereof wherein one or more double bonds occupy different positions within the various rings, and mixtures thereof, wherein:

J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and two J groups together may form a divalent derivative thereby forming a saturated or unsaturated ring;

J* is $=(C)_c=CR^*_2$, $=NR^*$, or $=O$, where R* is hydrogen, $C_{1-10}$ hydrocarbyl, N,N-di($C_{1-4}$ alkyl)amino, or halogen, and c is 0, 1 or 2; preferably J* is methylene or $=CF_2$;

A is the divalent remnant of an aromatic ring group (3); and

M* is hydrogen, an alkali metal or an alkaline earth metal halide.

Desirably, Cp, in the foregoing metal complexes of formula (II) is a polycyclic, fused ring ligand comprising at least: (1) a cyclopentadienyl ring by means of which said Cp is bonded to at least M, (2) a methanediyl or difluoromethanediyl substituted 7 membered polyatomic ring, and (3) one or more aromatic ring systems, with the proviso that said methanediyl or difluoromethanediyl substituted 7 membered ring (2), is fused to both the cyclopentadienyl ring (1), and said one or more aromatic ring systems (3), said Cp having up to 60 atoms other than hydrogen;

Preferred compounds (metal complexes) of formula (II) of the invention are those corresponding to the formula:

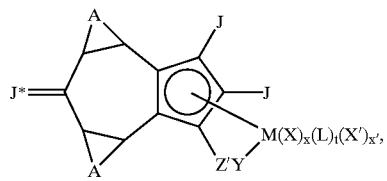
(IIa¹)

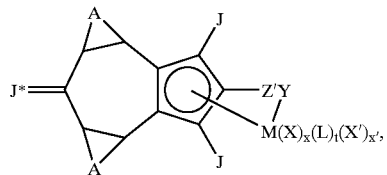
(IIb¹)

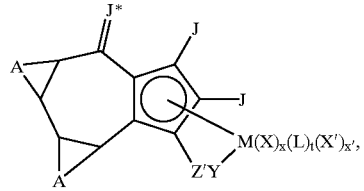
(IIc¹)

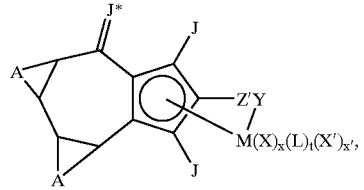
(IId¹)

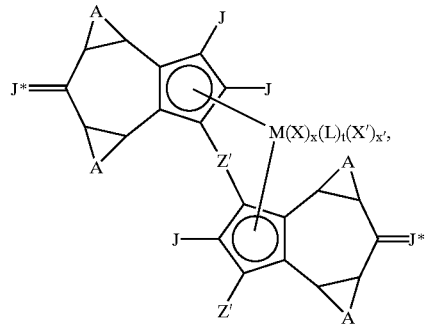
(IIa²)

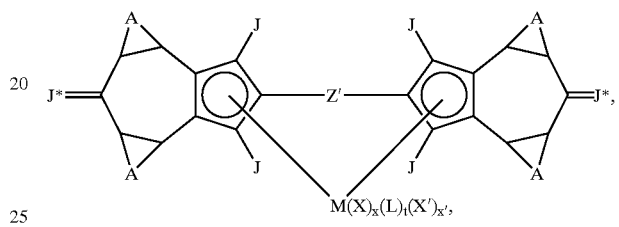
(IIb²)

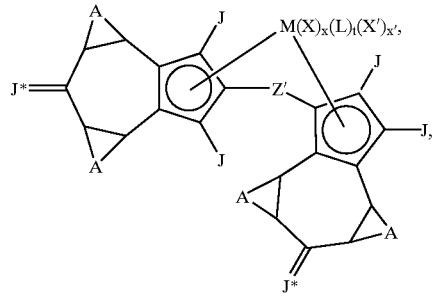
(IIab²)

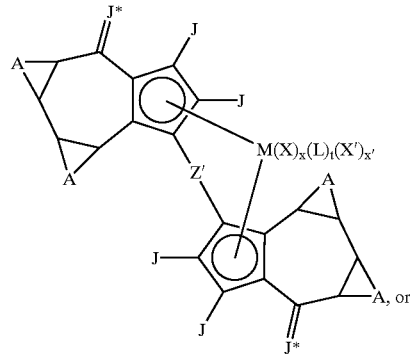
(IIc²)

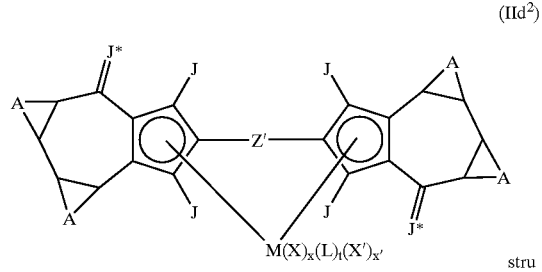
(IId²)

stru ctural isomers thereof, especially racemic isomers, and mixtures of the foregoing metal complexes, wherein:

J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and two J groups together may form a divalent derivative thereby forming a saturated or unsaturated ring;

$J^*$ is $=CR^*_2$; where $R^*$ is hydrogen, $C_{1-10}$ hydrocarbyl, or halide, preferably $J^*$ is methylene or $=CF_2$;

A is the divalent remnant of an aromatic ring group (3);

M is a Group 4 metal;

Y is —O—, —S—, —$NR^5$—, —$PR^5$—; —$NR^5_2$, or —$PR^5_2$;

Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;

$R^5$ each occurrence is independently hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$ each occurrence is independently hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;

X, L, L'', and X' are as previously defined;

x is 0, 1 or 2;

t is 0 or 1; and x' is 0 or 1.

In a desirable embodiment, when x is 2, x' is zero, M is in the +4 formal oxidation state (or M is in the +3 formal oxidation state if Y is —$NR^5_2$ or —$PR^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and x' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when x and x' are both 0, t is 1, M is in the +2 formal oxidation state, and L is a neutral, conjugated or nonconjugated diene, optionally substituted with one or more hydrocarbyl groups, said L having up to 40 carbon atoms and being bound to M by means of delocalized π-electrons thereof.

In the metal complexes, preferred L and L'' groups are carbon monoxide; phosphines, especially trimethylphosphine, triethylphosphine, triphenylphosphine and bis(1,2-dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including neutral diene L groups are those wherein the metal is in the +2 formal oxidation state.

Further in reference to the metal complexes, X preferably is desirably selected from the group consisting of hydro, halo, hydrocarbyl, silyl, and N,N-dialkylamino-substituted hydrocarbyl. The number of X groups depends on the oxidation state of M, whether Z is divalent or not and whether any neutral diene groups or divalent X' groups are present. The skilled artisan will appreciate that the quantity of the various substituents and the identity of Z are chosen to provide charge balance, thereby resulting in a neutral metal complex. For example, when Z is divalent, and x is zero, x' is two less than the formal oxidation state of M. When Z contains one neutral two electron coordinate-covalent bonding site, and M is in a formal oxidation state of +3, x may equal zero and x' equal 1, or x may equal 2 and x' equal zero. In a final example, if M is in a formal oxidation state of +2, Z may be a divalent ligand group, whereupon x and x' are both equal to zero and one neutral L ligand group may be present.

Highly preferred compounds of formula (I) are those wherein M* is hydrogen, sodium, potassium or lithium.

More highly preferred compounds and metal complexes according to the present invention correspond to the formulas:

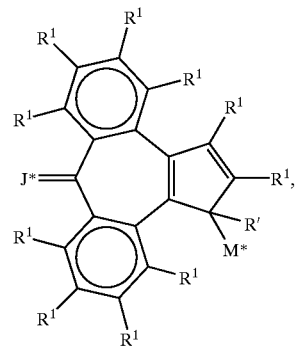

-continued

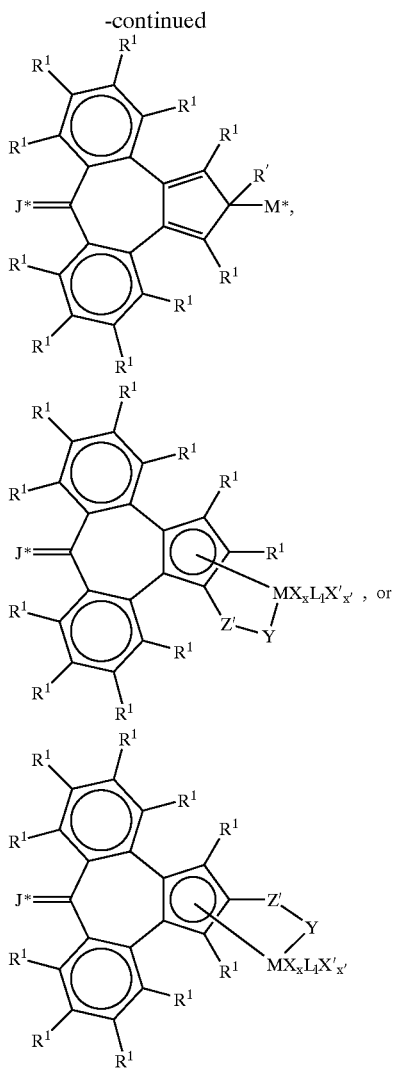

wherein,
M* is hydrogen, sodium, potassium or lithium;
M is titanium;
J* is methylene or difluoromethylene;
$R^1$ each occurrence is hydrogen or a hydrocarbyl, hydrocarbyloxy, dihydrocarbylamino, hydrocarbyleneamino, dihydrocarbylamino-substituted hydrocarbyl group, or hydrocarbyleneamino-substituted hydrocarbyl group of up to 20 atoms not counting hydrogen, and optionally two $R^1$ groups may be joined together;
Y is —O—, —S—, —$NR^5$—, —$PR^5$—; —$NR^5_2$, or —$PR^5_2$;
Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;
$R^5$ each occurrence is independently hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;
$R^6$ each occurrence is independently hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;
X, L, and X' are as previously defined;
x is 0, 1 or 2;
t is 0 or 1; and
x' is 0 or 1;

and, when x is 2, x' is zero, M is in the +4 formal oxidation state (or M is in the +3 formal oxidation state if Y is —$NR^5_2$ or —$PR^5_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and x' is 0, M is in the +3 formal oxidation state, and X is a stabilizing anionic ligand group selected from the group consisting of allyl, 2-(N,N-dimethylamino) phenyl, 2-(N,N-dimethylaminomethyl)phenyl, and 2-(N,N-dimethylamino)benzyl, and when x and x' are both 0, t is 1, M is in the +2 formal oxidation state, and L is a neutral, conjugated or nonconjugated diene, optionally substituted with one or more hydrocarbyl groups, said L having up to 40 carbon atoms and being bound to M by means of delocalized π-electrons thereof.

Most highly preferably, $R^1$ each occurrence is hydrogen,
Z is $NR^5$ wherein $R^5$ is $C_{1-10}$ alkyl or cycloalkyl, preferably t-butyl; and
Z' is dimethylsilane;
and, when x is 2, t and x' are both zero, M is in the +4 formal oxidation state, and X is independently each occurrence methyl, benzyl, or halide;
when x and t are zero, x' is one, and M is in the +4 formal oxidation state, X' is a 1,4-butadienyl group that forms a metallocyclopentene ring with M,
when x is 1, t and x' are zero, M is in the +3 formal oxidation state, and X is 2-(N,N-dimethylamino)benzyl; and
when x and x' are 0, t is 1, M is in the +2 formal oxidation state, and L is 1,4-diphenyl-1,3-butadiene or 1,3-pentadiene.

Specific examples of metal complexes of formula (II) according to the present invention include:

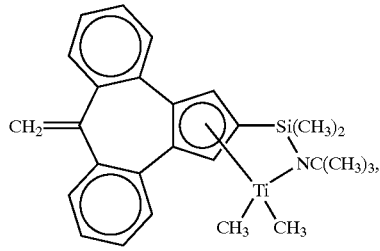

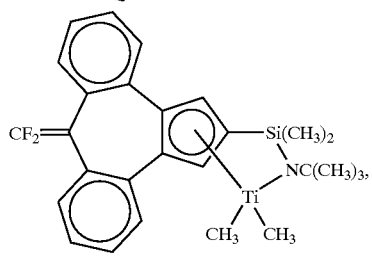

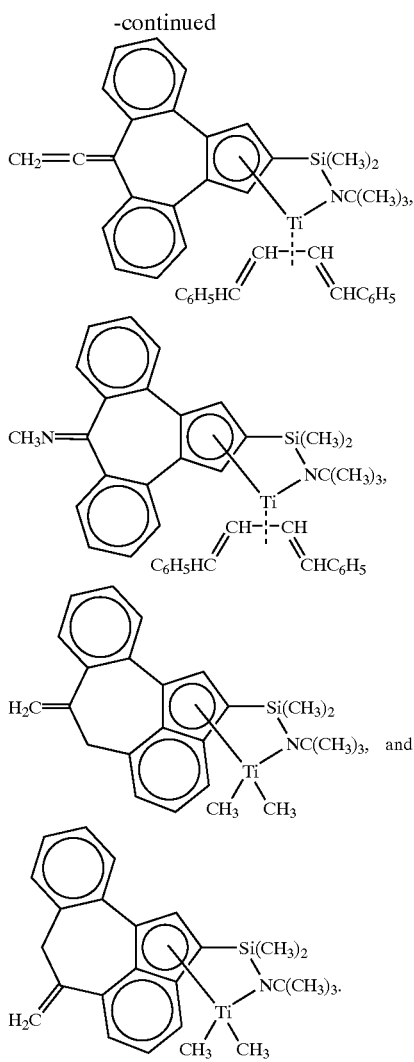

The compounds of the present invention are formed from the corresponding neutral methanediyl or difluoromethandiyl substituted azulene compound, which in turn are prepared by acetylation, carbonylating and ring closing processes. The neutral azulenes are prepared from dibenzosuberenone by bromination followed by dehydrobromination substantially according to the technique used in *J. Org. Chem.*, 37(26), 4294 (1972).

Illustrative metal complexes according to the present invention include:

(8-methylene-1,8-dihydrodibenzo[e,h]azulen-1-yl)-N-(1,1-dimethylethyl)dimethylsilanamide titanium (II) 1,4-diphenyl-1,3-butadiene,
(8-methylene-1,8-dihydrodibenzo[e,h]azulen-1-yl)-N-(1,1-dimethylethyl)dimethylsilanamide titanium (II) 1,3-pentadiene,
(8-methylene-1,8-dihydrodibenzo[e,h]azulen-1-yl)-N-(1,1-dimethylethyl)dimethylsilanamide titanium (III) 2-(N,N-dimethylamino)benzyl,
(8-methylene-1,8-dihydrodibenzo[e,h]azulen-1-yl)-N-(1,1-dimethylethyl)dimethylsilanamide titanium (IV) dichloride,
(8-methylene-1,8-dihydrodibenzo[e,h]azulen-1-yl)-N-(1,1-dimethylethyl)dimethylsilanamide titanium (IV) dimethyl,
(8-methylene-1,8-dihydrodibenzo[e,h]azulen-1-yl)-N-(1,1-dimethylethyl)dimethylsilanamide titanium (IV) dibenzyl,
(8-difluoromethylene-1,8-dihydrodibenzo[e,h]azulen-1-yl)-N-(1,1-dimethylethyl)dimethylsilanamide titanium (II) 1,4-diphenyl-1,3-butadiene,
(8-difluoromethylene-1,8-dihydrodibenzo[e,h]azulen-1-yl)-N-(1,1-dimethylethyl)dimethylsilanamide titanium (II) 1,3-pentadiene,
(8-difluoromethylene-1,8-dihydrodibenzo[e,h]azulen-1-yl)-N-(1,1-dimethylethyl)dimethylsilanamide titanium (III) 2-(N,N-dimethylamino)benzyl,
(8-difluoromethylene-1,8-dihydrodibenzo[e,h]azulen-1-yl)-N-(1,1-dimethylethyl)dimethylsilanamide titanium (IV) dichloride,
(8-difluoromethylene-1,8-dihydrodibenzo[e,h]azulen-1-yl)-N-(1,1-dimethylethyl)dimethylsilanamide titanium (IV) dimethyl,
(8-difluoromethylene-1,8-dihydrodibenzo[e,h]azulen-1-yl)-N-(1,1-dimethylethyl)dimethylsilanamide titanium (IV) dibenzyl,
(8-methylene-1,8-dihydrodibenzo[e,h]azulen-2-yl)-N-(1,1-dimethylethyl)dimethylsilanamide titanium (II) 1,4-diphenyl-1,3-butadiene,
(8-methylene-1,8-dihydrodibenzo[e,h]azulen-2-yl)-N-(1,1-dimethylethyl)dimethylsilanamide titanium (II) 1,3-pentadiene,
(8-methylene-1,8-dihydrodibenzo[e,h]azulen-2-yl)-N-(1,1-dimethylethyl)dimethylsilanamide titanium (III) 2-(N,N-dimethylamino)benzyl,
(8-methylene-1,8-dihydrodibenzo[e,h]azulen-2-yl)-N-(1,1-dimethylethyl)dimethylsilanamide titanium (IV) dichloride,
(8-methylene-1,8-dihydrodibenzo[e,h]azulen-2-yl)-N-(1,1-dimethylethyl)dimethylsilanamide titanium (IV) dimethyl,
(8-methylene-1,8-dihydrodibenzo[e,h]azulen-2-yl)-N-(1,1-dimethylethyl)dimethylsilanamide titanium (IV) dibenzyl,
(8-difluoromethylene-1,8-dihydrodibenzo[e,h]azulen-2-yl)-N-(1,1-dimethylethyl)dimethylsilanamide titanium (II) 1,4-diphenyl-1,3-butadiene,
(8-difluoromethylene-1,8-dihydrodibenzo[e,h]azulen-2-yl)-N-(1,1-dimethylethyl)dimethylsilanamide titanium (II) 1,3-pentadiene,
(8-difluoromethylene-1,8-dihydrodibenzo[e,h]azulen-2-yl)-N-(1,1-dimethylethyl)dimethylsilanamide titanium (III) 2-(N,N-dimethylamino)benzyl,
(8-difluoromethylene-1,8-dihydrodibenzo[e,h]azulen-2-yl)-N-(1,1-dimethylethyl)dimethylsilanamide titanium (IV) dichloride,
(8-difluoromethylene-1,8-dihydrodibenzo[e,h]azulen-2-yl)-N-(1,1-dimethylethyl)dimethylsilanamide titanium (IV) dimethyl,
(8-difluoromethylene-1,8-dihydrodibenzo[e,h]azulen-2-yl)-N-(1,1-dimethylethyl)dimethylsilanamide titanium (IV) dibenzyl, and mixtures thereof, especially mixtures of positional isomers.

The skilled artisan will recognize that additional members of the foregoing list, obtainable by substitution of known ligands or different Group 3–10 metals for those specifically named, are also included within the invention. Moreover, it should also be recognized that all possible electronic distributions within the molecule, such as $\eta^3$, $\eta^4$ or $\eta^5$ are intended to be included by the foregoing named compounds.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri (hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. A preferred ion forming compound is a tri($C_{1-20}$-hydrocarbyl)ammonium salt of a tetrakis (fluoroaryl)borate, especially a tetrakis(pentafluorophenyl)borate. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and U.S. Ser. No. 09/251,664, filed Feb. 17, 1999 now abandoned (WO99/42467).

Combinations of neutral Lewis acids, especially the combination of a trialkylaluminum compound having from 1 to 4 carbons in each alkyl group and a halogenated tri (hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluorophenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

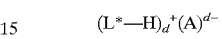

wherein:
L* is a neutral Lewis base;
$(L^*-H)^+$ is a conjugate Bronsted acid of L*;
$A^{d-}$ is a noncoordinating, compatible anion having a charge of d−, and
d is an integer from 1 to 3.
More preferably $A^{d-}$ corresponds to the formula:

wherein:
M' is boron or aluminum in the +3 formal oxidation state; and
Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

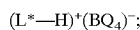

wherein:
L* is as previously defined;
B is boron in a formal oxidation state of 3; and
Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkyl-ammonium- or dialkylarylammonium-salts containing one or more $C_{12-40}$ alkyl groups. The latter cocatalysts have been found to be particularly suitable for use in combination with not only the present metal complexes but other Group 4 metallocenes as well.

Illustrative, but not limiting, examples of boron compounds which may be used as an activating cocatalyst in the preparation of the improved catalysts of this invention (as well as previously known Group 4 metal catalysts) are tri-substituted ammonium salts such as:

trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyltetradecylammonium tetrakis(pentafluorophenyl)borate,
dimethylhexadecylammonium tetrakis(pentafluorophenyl)borate,
dimethyloctadecylammonium tetrakis(pentafluorophenyl)borate,
methylditetradecylammonium tetrakis(pentafluorophenyl)borate,
methylditetradecylammonium(hydroxyphenyl)tris(pentafluorophenyl)borate,
methylditetradecylammonium (diethylaluminoxyphenyl)tris(pentafluorophenyl)borate,
methyldihexadecylammonium tetrakis(pentafluorophenyl)borate,
methyldihexadecylammonium(hydroxyphenyl)tris(pentafluorophenyl)borate,
methyldihexadecylammonium (diethylaluminoxyphenyl)tris(pentafluorophenyl)borate,
methyldioctadecylammonium tetrakis(pentafluorophenyl)borate,
methyldioctadecylammonium(hydroxyphenyl)tris(pentafluorophenyl)borate,
methyldioctadecylammonium (diethylaluminoxyphenyl)tris(pentafluorophenyl)borate,
methyldioctadecylammonium tetrakis(pentafluorophenyl)borate,
phenyldioctadecylammonium tetrakis(pentafluorophenyl)borate,
phenyldioctadecylammonium(hydroxyphenyl)tris(pentafluorophenyl)borate,
phenyldioctadecylammonium (diethylaluminoxyphenyl)tris(pentafluorophenyl)borate,
(2,4,6-trimethylphenyl)dioctadecylammonium tetrakis(pentafluorophenyl)borate,
(2,4,6-trimethylphenyl)dioctadecylammonium (hydroxyphenyl)tris(pentafluorophenyl)-borate,
(2,4,6-trimethylphenyl)dioctadecylammonium (diethylaluminoxyphenyl) tris(pentafluorophenyl)borate,
(2,4,6-trifluorophenyl)dioctadecylammonium tetrakis(pentafluorophenyl)borate,
(2,4,6-trifluorophenyl)dioctadecylammonium (hydroxyphenyl)tris(pentafluorophenyl)-borate,
(2,4,6-trifluorophenyl)dioctadecylammonium (diethylaluminoxyphenyl)tris(pentafluoro-phenyl) borate,
(pentafluorophenyl)dioctadecylammonium tetrakis(pentafluorophenyl)borate,
(pentafluorophenyl)dioctadecylammonium (hydroxyphenyl)tris(pentafluorophenyl)-borate,
(pentafluorophenyl)dioctadecylammonium (diethylaluminoxyphenyl)tris(pentafluoro-phenyl) borate,
(p-trifluoromethylphenyl)dioctadecylammonium tetrakis(pentafluorophenyl)borate,
(p-trifluoromethylphenyl)dioctadecylammonium (hydroxyphenyl)tris(pentafluoro-phenyl)borate,
(p-trifluoromethylphenyl)dioctadecylammonium (diethylaluminoxyphenyl)tris(penta-fluorophenyl) borate,
p-nitrophenyldioctadecylammonium tetrakis(pentafluorophenyl)borate,
p-nitrophenyldioctadecylammonium (hydroxyphenyl)tris(pentafluorophenyl)borate,
p-nitrophenyldioctadecylammonium (diethylaluminoxyphenyl)tris(pentafluorophenyl)borate,
and mixtures of the foregoing, dialkyl ammonium salts such as:
di-(i-propyl)ammonium tetrakis(pentafluorophenyl)borate, methyloctadecylammonium tetrakis(pentafluorophenyl)borate, methyloctadodecylammonium tetrakis(pentafluorophenyl)borate, and dioctadecylammonium tetrakis(pentafluorophenyl)borate;

tri-substituted phosphonium salts such as:
triphenylphosphonium tetrakis(pentafluorophenyl)borate, methyldioctadecylphosphonium tetrakis(pentafluorophenyl)borate, and tri(2,6-dimethylphenyl)phosphonium tetrakis(pentafluorophenyl)borate;

di-substituted oxonium salts such as:
diphenyloxonium tetrakis(pentafluorophenyl)borate, di(o-tolyl)oxonium tetrakis(pentafluorophenyl)borate, and di(octadecyl)oxonium tetrakis(pentafluorophenyl)borate;

di-substituted sulfonium salts such as:
di(o-tolyl)sulfonium tetrakis(pentafluorophenyl)borate, and methylcotadecylsulfonium tetrakis(pentafluorophenyl)borate.

Preferred trialkylammonium cations are methyldioctadecylammonium and dimethyloctadecylammonium. The use of the above Bronsted acid salts as activating cocatalysts for addition polymerization catalysts is known in the art, having been disclosed in U.S. Pat. Nos. 5,064,802, 5,919,983, 5,783,512 and elsewhere. Preferred dialkylarylammonium cations are fluorophenyldioctadecylammonium-, perfluorophenyldioctacecylammonium- and p-trifluoromethylphenyldi(octadecyl)ammonium cations. It should be noted that certain of the cocatalysts, especially those containing a hydroxyphenyl ligand in the borate anion, may require the addition of a Lewis acid, especially a trialkylaluminum compound, to the polymerization mixture or the catalyst composition, in order to form the active catalyst composition.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^{+}$ or $Pb^{+2}$. Preferred embodiments of $A^{d-}$ are those anions previously defined with respect to the Bronsted acid containing activating cocatalysts, especially tetrakis (pentafluorophenyl)borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

wherein:

©⁺ is a $C_{1-20}$ carbenium ion; and

A⁻ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

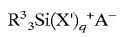

wherein:

$R^3$ is $C_{1-10}$ hydrocarbyl, and X', q and A⁻ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula:

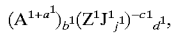

wherein:

$A^1$ is a cation of charge $+a^1$, $Z^1$ is an anion group of from 1 to 50, preferably 1 to 30 atoms, not counting hydrogen atoms, further containing two or more Lewis base sites;

$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1$, $b^1$, $c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

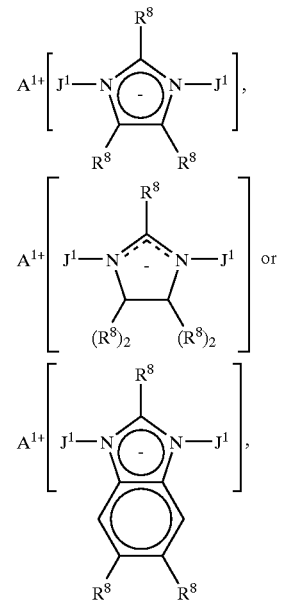

wherein:

$A^{1+}$ is a monovalent cation as previously defined, and preferably is a trihydrocarbyl ammonium cation, containing one or two $C_{10-40}$ alkyl groups, especially the methylbis (tetradecyl)ammonium- or methylbis(octadecyl) ammonium-cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris (pentafluorophenyl)aluminane.

Examples of these catalyst activators include the trihydrocarbylammonium-, especially, methylbis(tetradecyl) ammonium- or methylbis(octadecyl)ammonium- salts of: bis(tris(pentafluorophenyl)borane)imidazolide, bis(tris (pentafluorophenyl)borane)-2-undecylimidazolide, bis (tris(pentafluorophenyl)borane)-2-heptadecylimidazolide, bis(tris(pentafluorophenyl) borane)-4,5-bis(undecyl)imidazolide, bis(tris (pentafluorophenyl)borane)-4,5-bis(heptadecyl) imidazolide, bis(tris(pentafluorophenyl)borane) imidazolinide, bis(tris(pentafluorophenyl)borane)-2-undecylimidazolinide, bis(tris(pentafluorophenyl) borane)-2-heptadecylimidazolinide, bis(tris (pentafluorophenyl)borane)-4,5-bis(undecyl) imidazolinide, bis(tris(pentafluorophenyl)borane)-4,5-bis (heptadecyl)imidazolinide, bis(tris(pentafluorophenyl) borane)-5,6-dimethylbenzimidazolide, bis(tris (pentafluorophenyl)borane)-5,6-bis(undecyl) benzimidazolide, bis(tris(pentafluorophenyl)alumane) imidazolide, bis(tris(pentafluorophenyl)alumane)-2-undecylimidazolide, bis(tris(pentafluorophenyl) alumane)-2-heptadecylimidazolide, bis(tris (pentafluorophenyl)alumane)-4,5-bis(undecyl) imidazolide, bis(tris(pentafluorophenyl)alumane)-4,5-bis (heptadecyl)imidazolide, bis(tris(pentafluorophenyl) alumane)imidazolinide, bis(tris(pentafluorophenyl) alumane)-2-undecylimidazolinide, bis(tris (pentafluorophenyl)alumane)-2-heptadecylimidazolinide, bis(tris(pentafluorophenyl)alumane)-4,5-bis(undecyl)

imidazolinide, bis(tris(pentafluorophenyl)alumane)-4,5-bis(heptadecyl)imidazolinide, bis(tris(pentafluorophenyl)alumane)-5,6-dimethylbenzimidazolide, and bis(tris(pentafluorophenyl)alumane)-5,6-bis(undecyl)benzimidazolide.

A further class of suitable activating cocatalysts include cationic Group 13 salts corresponding to the formula:

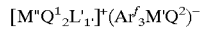

wherein:
M" is aluminum, gallium, or indium;
M' is boron or aluminum;
$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;
$Q^2$ is an alkyl group, optionally substituted with one or more cycloalkyl or aryl groups, said $Q^2$ having from 1 to 30 carbons;
L' is a monodentate or polydentate Lewis base, preferably L' is reversibly coordinated to the metal complex such that it may be displaced by an olefin monomer, more preferably L' is a monodentate Lewis base;
1' is a number greater than zero indicating the number of Lewis base moieties, L', and
$Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris (fluoroaryl)borates corresponding to the formula: $[M"Q^1{}_2L'{}_{1'}]^+(Ar^f{}_3BQ^{2-})$, where wherein M" is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl)borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefin compounds, including ethylidene norbornene, 1,4-hexadiene, norbornadiene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from $1:10^6$ to $1:10^3$, more preferably from $1:10^6$ to $1:10^4$.

In most polymerization reactions the molar ratio of catalyst:polymerizable compounds employed is from $10^{-12}:1$ to $10^{-1}:1$, more preferably from $10^{-9}:1$ to $10^{-5}:1$.

Suitable solvents use for solution polymerization are liquids that are substantially inert under process conditions encountered in their usage. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500.

The catalysts of the present invention are particularly advantageous for the production of ethylene homopolymers and ethylene/α-olefin copolymers having high levels of long chain branching. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In a preferred embodiment, a heterogeneous catalyst is prepared by reacting an inorganic compound, preferably a tri($C_{1-4}$ alkyl)aluminum compound, with an activating cocatalyst, especially an ammonium salt of a hydroxyaryl(trispentafluorophenyl)borate, such as an ammonium salt of (4-hydroxy-3,5-ditertiarybutylphenyl)tris(pentafluorophenyl)borate or (4-hydroxyphenyl)-tris(pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise, the α-olefin monomer or a mixture of different α-olefin monomers may be used in whole or part as the diluent. Most preferably, at least a major part of the diluent comprises the α-olefin monomer or monomers to be polymerized. A dispersant, particularly an elastomer, may be dissolved in the diluent utilizing techniques known in the art, if desired.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas, such as, for example, nitrogen.

The polymerization may be carried out as a batchwise or a continuous polymerization process. A continuous process is preferred, in which event catalyst, ethylene, comonomer, and optionally solvent, are continuously supplied to the reaction zone, and polymer product continuously removed therefrom.

Without limiting in any way the scope of the invention, one means for carrying out such a polymerization process is as follows: In a stirred-tank reactor, the monomers to be polymerized are introduced continuously, together with solvent and an optional chain transfer agent. The reactor contains a liquid phase composed substantially of monomers, together with any solvent or additional diluent and dissolved polymer. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours.

Ethylene homopolymers and ethylene/α-olefin copolymers are particularly suited for preparation according to the invention. Generally such polymers have densities from 0.85 to 0.96 g/ml. Typically the molar ratio of α-olefin comonomer to ethylene used in the polymerization may be varied in order to adjust the density of the resulting polymer. When producing materials with a density range of from 0.91 to 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than about 0.5, preferably less than 0.2, more preferably less than 0.05, even more preferably less than 0.02 and may even be less than 0.01.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc.

All solvents were purified using the technique disclosed by Pangborn et al, *Organometallics*, 15, 1518–1520, (1996). $^1$H and $^{13}$C NMR shifts were referenced to internal solvent resonances and are reported in ppm relative to TMS. All J values are given in Hz. Mass spectra were obtained via EI ionization mode. Syntheses were conducted according to the following schematic representation:

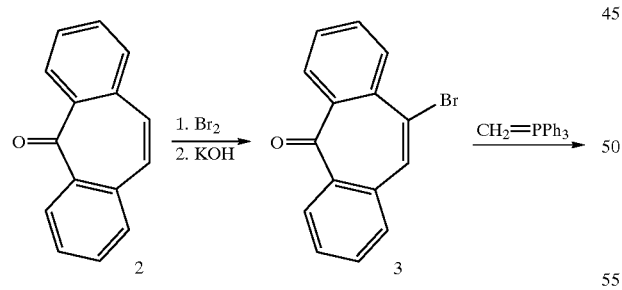

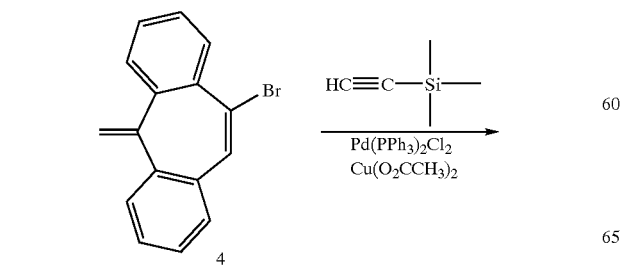

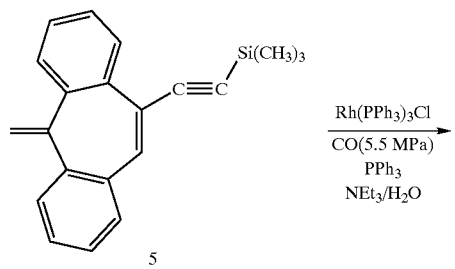

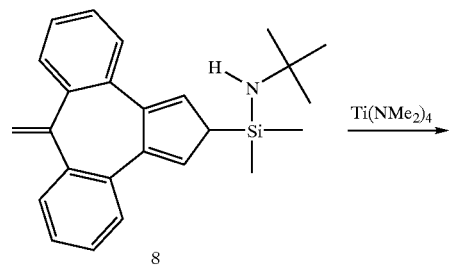

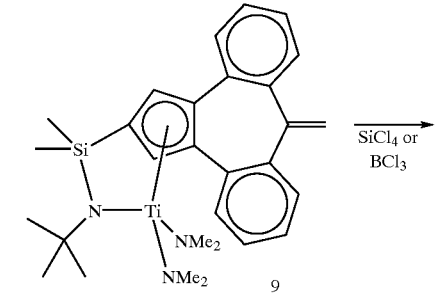

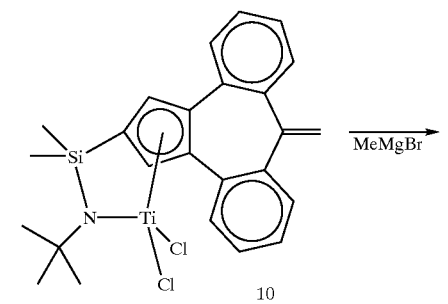

-continued

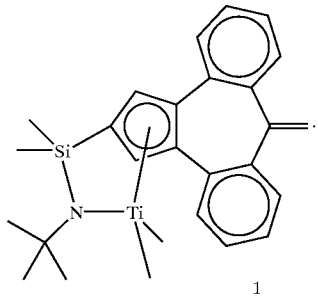

1

Example 1

(8-methylene-2,8-dihydrodibenzo[e,h]azulen-2-yl)-N-(1,1-dimethylethyl)-dimethylsilanamide titanium di(N,N-dimethyl)amide (9)

Preparation of 10-bromo-5-methylene-5H-dibenzo[a,d]cycloheptene (4)

In a glove box, methyltriphenylphosphonium bromide (8.22 g, 23 mmol, 357.23 g/mol) was dissolved in 150 mL of THF in a flame-dried flask, and n-BuLi (9.21 mL, 23 mmol, 2.5 M in hexane) was added drop wise. The yellow mixture was stirred at ambient temperature for 30 min. and 10-bromo-5H-dibenzo[a,d]cyclohepten-5-one (6.55 g, 23 mmol, 285.14 g/mol) was added as a THF solution. The mixture was stirred and heated at reflux for two days. The cooled solution was taken out of glove box and diluted with 100 mL of hexane. A small amount of water was added to quench the excess reagent, and the mixture was filtered through a plug of silica gel. The silica was rinsed with additional hexane, and the filtrate was concentrated under reduced pressure. The residue was purified by chromatography on silica gel and eluted with ether/hexane (1:1) mixture by volume. Solvent was removed to yield 5.53 g (85 percent, 283.17 g/mol) of the title compound as a pale yellow oil that crystallized upon standing.

$^1$H NMR (CDCl$_3$, 300 MHz, δ(ppm)): 7.89 (m, 1H), 7.58 (s, 1H), 7.39–7.23 (m, 7H), 5.34 (s, 2H).

$^{13}$C NMR (CDCl$_3$, 75.45 MHz, δ(ppm)): 150.0, 142.0, 141.5, 134.5, 133.9, 133.0, 130.4, 130.2, 130.0, 128.4, 128.1, 127.8, 127.7, 125.4, 120.1.

Preparation of trimethyl[2-(5-methylene-5H-dibenzo[a,d]cyclohepten-10-yl)ethynyl)silane (5)

To a stirred mixture of 4 (5.66 g, 20 mmol), dichlorobis(triphenylphosphine) palladium(II) (0.7 g, 1 mmol), copper (II) acetate hydrate (0.18 g, 1 mmol) and triphenylphosphine (0.52 g, 2 mmol) in 40 mL of diisopropyl amine was added trimethylsilyl acetylene (2.16 g, 22 mmol) and heated to reflux. On refluxing for an hour the mixture turns dark and solidifies. The reaction mixture was diluted with 50 mL of hexane and filtered. The filtrate was concentrated under reduced pressure and the residue was chromatographed over silica gel with hexane/methylene chloride (9:1 by volume) as eluant to yield 2.88 g (50 percent) of trimethyl[2-(5-methylene-5H-dibenzo[a,d]cyclohepten-10-yl)ethynyl)silane, 5, as a yellow oil.

$^1$H NMR (CDCl$_3$, 300 MHz, δ (ppm)): 0.29 (s, 9H), 5.26 (d, J=1.2 Hz, 2H), 7.35–7.37 (m, 6H), 7.37–7.38 (m, 2H);

$^{13}$C NMR (CDCl$_3$, 75.45 MHz; δ (ppm)): 0.0, 95.2, 106.8, 119.9, 124.2, 127.4, 127.4, 127.5, 128.0, 128.2, 129.3, 133.0, 138.1, 141.6, 141.8, 150.1;

MS: m/z (%): 300 (M$^+$), 285.

Preparation of 8-methylene-3,8-dihydrodibenzo[e,h]azulen-1(2H)-one (6)

A 300 mL Parr reactor was charged with compound 5 (3.0 g, 10 mmol), chlorotris(triphenylphosphine)rhodium (0.092 g, 0.10 mmol), triethyl amine (2.02 g, 20 mmol), triphenylphosphine (0.52 g, 2.0 mmol), water (0.72 g, 4.0 mmol) and 100 mL of THF. The reactor was pressurized with carbon monoxide to 800 psi and heated to 165° C. for 16 hr. The reaction mixture was worked up by concentrating under reduced pressure and the residue was purified by chromatography over silica gel with heane/methylene chloride (2/8) as eluant to yield 1.2 g (47%) of 8-methylene-3,8-dihydrodibenzo[e,h]azulen-1(2H)-one, 6, as a low melting yellow solid.

$^1$H NMR (CDCl$_3$, 300 MHz, δ (ppm)): 2.57–2.66 (m, 3H), 3.34–3.44 (m, 1H), 5.22–5.26 (m, 2H), 7.29–7.51 (m, 6H), 7.94–7.97 (m, 2H);

$^{13}$C NMR (CDCl$_3$, 75.45 MHz, δ (ppm)): 28.2, 34.5, 119.7, 125.6, 127.0, 127.4, 127.5, 128.0, 131.4, 132.6, 137.2, 142.1, 143.1, 150.0, 166.8, 207.1, MS: m/z (%): 258 (M$^+$), 229, 215.

Preparation of 8-methylene-1,8-dihydrodibenzo[e,h]azulene, 7.

To a stirred solution of the ketone 6 (1.0 g, 4.0 mmol) in methylene chloride/methanol (3/1 by volume, 40 mL) was added sodium borohydride (1.0 g, 27 mmol). The reaction was monitored by thin layer chromatography (tlc) for the disappearance of the starting ketone, 6. After 1 hr the reaction was worked up diluting with water (30 mL) and the organic layer was dried over anhydrous magnesium sulfate and concentrated under reduced pressure to yield a yellow solid. The yellow solid as dissolved in benzene (50 mL) containing p-toluenesulfonic acid (10 mg) and heated to 45° C. The reaction mixture was monitored by tlc for the disappearance of the alcohol (45 min). The reaction was worked up by washing with saturated aqueous sodium bicarbonate solution (30 mL), dried over anhydrous magnesium sulfate and concentrated under reduced pressure to yield 0.66 g (68 percent) of the 8-methylene-1,8-dihydrodibenzo[e,h]azulene, 7, as a yellow oil.

$^1$H NMR (CDCl$_3$, 300 MHz, δ (ppm)): 3.42 (d, J=24 Hz, 1H), 3.88 (d, J=24 Hz, 1H), 5.24 (dd, J=2 Hz, 3 Hz, 2H), 6.56 (d, J=6 Hz, 1H), 6.97 (d, J=6 Hz, 1H), 7.27–7.50 (m, 8H)

$^{13}$C NMR (CDCl$_3$, 75.45 MHz, δ (ppm)): 44.3, 119.9, 125.9, 126.2, 127.4, 127.9, 127.9, 128.0, 128.2, 128.3, 132.5, 132.6, 133.4, 134.8, 140.8, 141.1, 141.2, 141.4, 151.5

MS: m/z (%): 242 (M$^+$), 226, 215, 119.

Preparation of N-(tert-butyl)(dimethyl)(8-methylene-1,8-dihydrodibenzo[e,h]azulen-2-ylsilanamine (8)

8-methylene-1,8-dihydrodibenzo[e,h]azulene, 7 (0.78 g, 3.2 mmol) was stirred in toluene (15 mL) as KN(TMS)$_2$ (0.64 g, 3.2 mmol) was added as solid in portions. This mixture was allowed to stir at room temperature over night, resulting in yellow slurry. Hexane was added to induce further precipitation. After cooling at −25° C. over night, the solid was filtered, washed with hexane and, dried in vacuo. The resulting yellow solid was redissolved in THF (30 mL) and then added to neat Si(CH$_3$)$_2$Cl$_2$ (4.16 g, 32.1 mmol) drop-wise with stirring. After addition, the volatiles were removed under vacuum and the residue was redissolved in THF and excess t-butyl amine (0.52 g, 7 mmol) was added. The reaction mixture was allowed to stir over night. The volatiles were removed and the residual was extracted and filtered using toluene. Solvent removal under vacuum resulted in the isolation of the desired compound as the major isomeric product as pale yellow oil (1.07 g, 90 percent yield).

[N-(tert-butyl)(dimethyl)(8-methylene-1,8-dihydrodibenzo[e,h]azulen-2-yl) silanamide]bis(dimethylamido)titanium (9)

The isomeric mixture including 8 (0.673 g, 1.81 mmol) was dissolved in 70 mL n-octane and titanium tetrakis (dimethylamide) (0.406 g, 1.81 mmol) was added. The solution was heated to and stirred at reflux for 5 days. The solution turned red. A small aliquot of the cooled solution was removed and volatile components of this aliquot were removed under reduced pressure. The $^1$H NMR spectra of the residue are consistent with complete conversion of the ligand to [N-(tert-butyl)(dimethyl)(8-methylene-1,8-dihydrodibenzo[e,h]azulen-2-yl)silanamide]bis(dimethylamido)titanium, 9, and a small quantity of unreacted $Ti(NMe_2)_4$.

$^1$H NMR ($C_6D_6$, 300 MHz; δ (ppm)): 0.62 (s, 6H); 1.30 (s, 9H); 2.64 (s,12H); 5.17 (s, 2H); 6.41 (s, 2H); 7.05–7.10 (m, 4H); 7.27–7.30 (m, 2H); 7.45–7.48 (m, 2H).

Example 2

[N-(tert-butyl)(dimethyl)(8-methylene-1,8-dihydrodibenzo[e,h]azulen-2-yl)silanamide]titanium dichloride To the remaining solution of [N-(tert-butyl)(dimethyl)(8-methylene-1,8-dihydrodibenzo[e,h]azulen-2-yl)silanamide] titanium dichloride in n-octane (Example 1) was added neat $SiCl_4$ (0.5 mL, 4 mmol). An orange precipitate formed immediately. After one hour the solid was collected by vacuum filtration. Volatile materials were removed from the solid under reduced pressure to give 0.411 g of material. Proton NMR spectroscopy showed low levels of impurities in the desired compound. This was purified by dissolving in a hexanes/toluene solution (70/30 by volume), filtering, and removing the volatile materials under reduced pressure. Evaporative cooling caused the product to crystallize and 0.296 of a micro-crystalline solid was isolated.

Volatile materials were removed from the first n-octane filtrate under reduced pressure. The residue was slurried in 15 mL hexanes. An orange solid was collected by vacuum filtration and dried in vacuo to give 0.106 g of product.

The combined yield is 0.402 g, 45 percent. NMR spectra of both materials are consistent with very pure samples of [N-(tert-butyl)(dimethyl)(8-methylene-1,8-dihydrodibenzo[e,h]azulen-2-yl)silanamide]titanium dichloride.

$^1$H NMR ($C_6D_6$, 300 MHz; δ (ppm)): 0.36 (s, 6H); 1.38 (s, 9H); 5.50 (s, 2H); 6.66 (s, 2H); 7.07–7.18 (m, 4H); 7.29–7.34 (m, 2H); 7.41–7.46 (m, 2H)

$^{13}$C NMR ($C_6D_6$, 75.45 MHz; δ (ppm)): −0.12, 32.5, 64.1, 110.4, 123.9, 124.3, 128.3 (obscured by a solvent peak), 129.0, 130.0, 131.1, 139.7, 143.4, 149.6

HRMS (EI): calculated for $(M-CH_3)^+$ ($C_{24}H_{24}NCl_2TiSi$), 472.0538; found 472.0544

Example 3

[N-(tert-butyl)(dimethyl)(8-methylene-1,8-dihydrodibenzo[e,h]azulen-2-yl)silanamide]dimethyl titanium (1)

To a solution of [N-(tert-butyl)(dimethyl)(8-methylene-1,8-dihydrodibenzo[e,h]azulen-2-yl)silanamide]titanium dichloride, 10 (0.296 g, 0.606 mmol) in diethylether was added 3.0 M methyl magnesium bromide in diethylether (0.45 mL, 1.4 mmol). The solution darkened and a precipitate formed immediately. After stirring the mixture for two hours, the volatiles were removed under reduced pressure. The residue was extracted twice with a total of 60 mL hexanes. The hexanes extracts were filtered and the volatiles were removed from the combined filtrate under reduced pressure to give 0.146 g of a yellow micro-crystalline solid (54 percent yield). The NMR spectra are consistent with [N-(tert-butyl)(dimethyl)(8-methylene-1,8-dihydrodibenzo[e,h]azulen-2-yl)silanamide]dimethyltitanium, 1.

$^1$H NMR ($C_6D_6$, 300 MHz; δ (ppm)): 0.38 (s, 6H); 0.53 (s, 6H); 1.52 (s, 9H); 5.24 (s, 2H); 6.29 (s, 2H); 7.08–7.16 (m, 4H); 7.29–7.36 (m, 2H); 7.54–7.61 (m, 2H).

$^{13}$C NMR ($C_6D_6$, 75.45 MHz; δ (ppm)): 0.55, 34.1, 56.5, 59.2, 105.6, 119.7, 121.4, 127.7 and 127.9 (both obscured by solvent peaks), 128.4, 128.7, 132.3, 134.1, 141.3, 151.7.

Polymerization General Conditions

Mixed alkanes and liquid olefins are purified by sparging with purified nitrogen followed by passage through columns containing alumina (A-2, available from LaRoche Inc.) and Q5 reactant (available from Englehard Chemicals Inc.) at 50 psig using a purified nitrogen pad. All transfers of solvents and solutions described below are accomplished using a gaseous pad of dry, purified nitrogen or argon. Gaseous feeds to the reactor are purified by passage through columns of A-204 alumina (available from LaRoche Inc.) and Q5 reactant. The aluminas are previously activated by treatment at 375° C. with nitrogen, and Q5 reactant is activated by treatment at 200° C. with 5 percent hydrogen in nitrogen.

Polymerization 1

A stirred, two-liter Parr reactor was charged with toluene and with purified styrene comonomer. Hydrogen (if used) was added as a molecular weight control agent by differential pressure expansion from a 75 mL addition tank at 275 psig (2.0 MPa). The reactor was heated to the desired temperature (either 90° C. or 130° C.) and saturated with ethylene at the desired pressure (1.50 MPa or 2.17 MPa). The appropriate amount of catalyst, (8-methylene-2,8-dihydrodibenzo-[e,h]azulen-2-yl)-N-(1,1-dimethylethyl)-dimethylsilanamide dimethyltitanium (Example 3), and cocatalyst as 0.005M solutions in toluene were premixed in a glovebox and transferred to a catalyst addition tank and injected into the reactor. (Periodic additions of catalyst/cocatalyst solution may be added during the course of the run, amounts indicated are totals.) The polymerization conditions were maintained during the run with ethylene on demand.

After the indicated reaction time, the resulting solution was removed from the reactor into a nitrogen purged collection vessel containing 100 ml of isopropyl alcohol and 20 ml of a 10 weight percent toluene solution of hindered phenol antioxidant (Irganox™ 1010 from Ciba Geigy Corporation) and phosphorus stabilizer (Irgafos™ 168 from Ciba Geigy Corporation). Polymers formed are dried in a programmed vacuum oven with a maximum temperature of 145° C. and a 20 hour heating period. The results are contained in Table 1.

TABLE 1

| Run | Cat. (μmol) | Cocatalyst (μmol) | Styrene (g) | Toluene (g) | Ethylene (MPa) | T. (° C.) | $H_2$ (kPa) | Time (minutes) | Yield (g) | eff.[3] | [Styrene][4] | Mw | Mw/Mn |
|---|---|---|---|---|---|---|---|---|---|---|---|---|---|
| 1 | 2.0 | TPFB[1] (6.0) | 456 | 433 | 1.50 | 90 | 345 | 6.5 | 296 | 3.17 | 40.9 | 87,000 | 3.0 |
| 2 | 1.0 | " (3.0) | " | " | " | " | " | 31 | 270 | 5.6 | 38.9 | 99,000 | 3.3 |
| 3 | 3.0 | " (6.0) | 201 | 674 | 2.17 | 130 | 0 | 16 | 97 | 0.7 | 16.3 | 134,000 | 2.1 |
| 4 | 2.5 | " (7.5) | " | 676 | " | " | " | " | 92 | 0.8 | 17.0 | 134,000 | 2.0 |
| 5 | 2.5 | DMTPB[2] (2.5) | " | 675 | " | " | " | " | 150 | 1.3 | 16.7 | 154,000 | 2.1 |

[1]-trispentafluorophenylborane
[2]-dioctadecylmethylammonium tetrakispentafluorophenylborate
[3]-efficiency, g polymer/ μg Ti
[4]-polymerized styrene content of polymer, mol percent Solution Ethylene Octene Polymerization Conditions:

The previous batch reactor polymerization conditions were substantially repeated using 740 g of mixed alkanes solvent and 118 g 1-octene comonomer. Hydrogen (Δ 23 psi, 160 kPa) was added by differential expansion from a 75 mL shot tank. The contents of the reactor was then heated to 140° C., under 500 psig (3.6 MPa) of ethylene pressure. The catalyst (as 0.0050 M solution in toluene) and cocatalyst (tris(perfluorophenyl)borane, 0.015 M) were combined in a one to three molar ratio in the glove box and transferred from the glove box to the catalyst shot tank through 1/16 in (0.16 cm) tubing using toluene to aid in the transfer. The catalyst tank was then pressurized to 700 psig (4.8 MPa) using nitrogen. After the contents of the reactor had stabilized at the desired run temperature of 140° C., the catalyst was injected into the reactor via a dip tube. The temperature was maintained by allowing cold glycol to pass through the internal cooling coils. The reaction was allowed to proceed for the desired time with ethylene provided on demand. Additional injections of catalyst prepared in the same manner may have been used. The contents of the reactor were then expelled into a 4 liter nitrogen purged vessel and quenched with 20 mL of a 10 weight percent toluene solution of antioxidant (Irganox™ 1010 from Ciba Corporation) and stabilizer (Irgafos™ 168 from Ciba Corporation). The reactor was then washed with 1200 mL of solvent at 160° C. prior to the next run. Volatile materials were removed from the polymers in a vacuum oven up to 145° C. overnight and cooled to at least 50° C. prior to removal from the oven. Results are contained in Table 2.

TABLE 2

Ethylene/Octene Polymerization

| Run | Catalyst (μmoles) | Run Time (min) | Yield (g) | Efficiency (g/μg Ti) | Density* g/ml | MMI** (dg/min) |
|---|---|---|---|---|---|---|
| 6 | Ex. 3 (3.0) | 16 | 28.8 | 0.20 | 0.930 | >100 |

*density is determined by displacement technique using methylethylketone
**micromelt index technique, calibrated using standards of known melt index

What is claimed is:

1. A polycyclic, fused ring compound corresponding to the formula:

$(Cp^*)_p$—M* (I) or $CpM(Z)_z(X)_x(L)_1(X')_{x'}$ (II), where Cp* is a polycyclic, fused ring ligand or inertly substituted derivative thereof comprising at least: (1) a cyclopentadienyl ring, (2) a 7 membered polyatomic ring, and (3) two aromatic ring systems, with the proviso that said 7 membered ring (2), is fused to both the cyclopentadienyl ring (1), and said two aromatic ring systems (3), at positions adjacent to the cyclopentadienyl ring thereby leaving one remaining ring position on the 7-membered ring which is substituted with a substituent group resulting in sp² hybridization on the ring atom bonded thereto, said Cp* having up to 60 atoms other than hydrogen;

p is 1 or 2;

when p is 1, M* is hydrogen, an alkali metal or an alkaline earth metal halide, and, when p is 2, M* is an alkaline earth metal; said M* being bound to at least one of the non-fused, ring-carbons of the cyclopentadienyl ring, (1);

Cp is the aromatic ligand group derived from Cp* by removal of M* from $(Cp^*)_p$—M*;

M is a metal selected from Groups 3–10 or the Lanthanide series of the Periodic Table of the Elements;

Z is either:

a) a cyclic ligand group containing delocalized π-electrons, including a second or third, fused, polycyclic ligand, Cp, said Z being bonded to M by means of delocalized π-electrons and optionally also covalently bonded to Cp through a divalent bridging group, Z', or b) a divalent moiety of the formula —Z'Y—, wherein, Z' is $SiR^6{}_2$, $CR^6{}_2$, $SiR^6{}_2SiR^6{}_2$, $CR^6{}_2CR^6{}_2$, $CR^6{=}CR^6$, $CR^6{}_2SiR^6{}_2$, $BR^6$, BR6L", or $GeR^6{}_2$;

Y is —O—, —S—, —$NR^5$—, —$PR^5$—; —$NR^5{}_2$, or —$PR^5{}_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5{}_2$, and combinations thereof, said $R^6$ having up to 20 non-hydrogen atoms, and optionally, two $R^6$ groups form a ring system;

L" is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;
z is 0, 1 or b 2;
x is 0, 1, 2, or 3;
t is a number from 0 to 2, and
x' is 0 or 1.
2. A compound or complex corresponding to the formula:
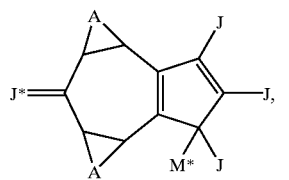
(Ia)
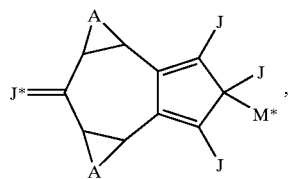
(Ib)
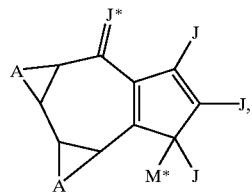
(Ic)
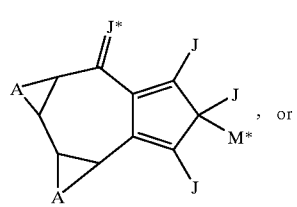
(Id)
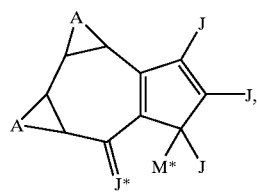
, or
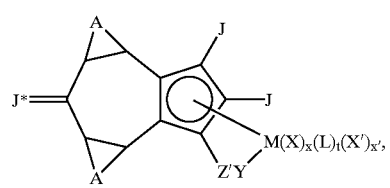
(Ie)
or the formula:
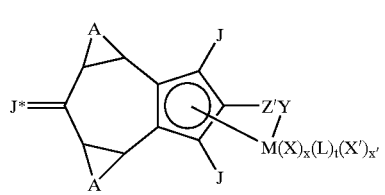
(IIa¹)
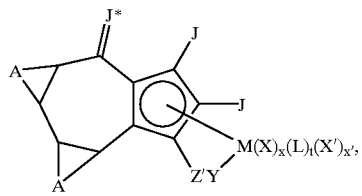
(IIb¹)
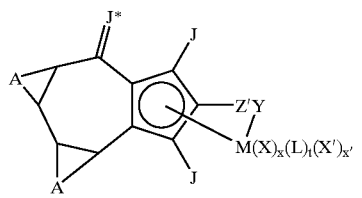
(IIc¹)
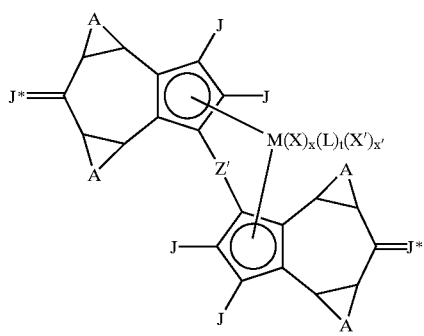
(IId¹)
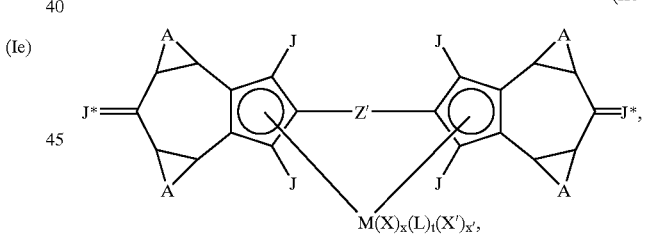
(IIa²)
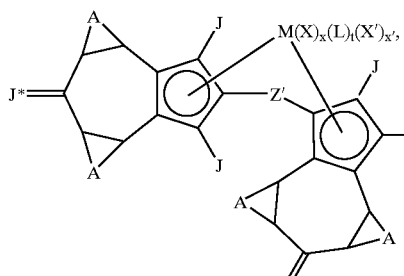
(IIb²)
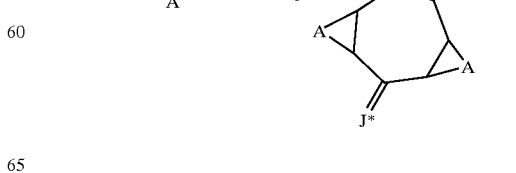
(IIab²)

33
-continued

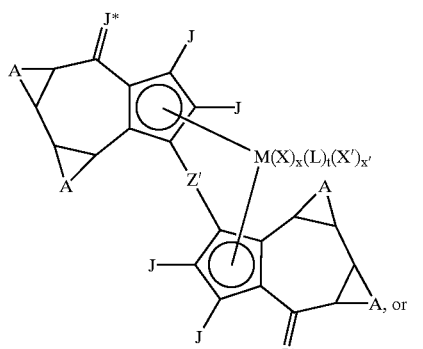

(IIc²)

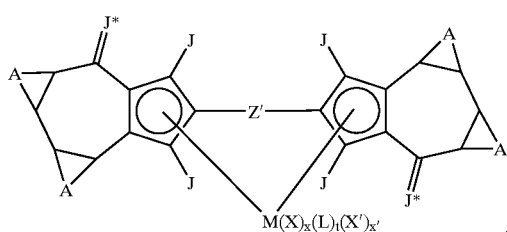

(IId²)

or mixtures thereof, wherein:

J independently each occurrence is hydrogen, hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbyleneamino, hydrocarbylimino, di(hydrocarbyl)phosphino, hydrocarbylenephosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said J group having up to 40 atoms not counting hydrogen atoms, and two J groups together may form a divalent derivative thereby forming a saturated or unsaturated ring;

J* is $=(C)_c=CR^*_2$, $=NR^*$, or $=O$, where $R^*$ is hydrogen, $C_{1-10}$ hydrocarbyl, N,N-di($C_{1-4}$ alkyl)amino, or halogen, and c is 0, 1 or 2;

A is the divalent remnant of an aromatic ring group (3);

M is a Group 4 metal;

Y is —O—, —S—, —NR⁵—, —PR⁵—; —NR⁵₂, or —PR⁵₂;

Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;

R⁵ each occurrence is independently hydrocarbyl, trihydrocarbylsilyl, or trihydrocarbylsilylhydrocarbyl, said R⁵ having up to 20 atoms other than hydrogen, and optionally two R⁵ groups or R⁵ together with Y form a ring system;

R⁶ each occurrence is independently hydrogen, or a member selected from hydrocarbyl, hydrocarbyloxy,

34 silyl, halogenated alkyl, halogenated aryl, —NR⁵₂, and combinations thereof, said R⁶ having up to 20 non-hydrogen atoms, and optionally, two R⁶ groups form a ring system;

M* is hydrogen, an alkali metal or an alkaline earth metal halide;

L'' is a monodentate or polydentate Lewis base optionally bonded to R⁶;

X is hydrogen or a monovalent anionic ligand group having up to 60 atoms not counting hydrogen:

L independently each occurrence is a neutral ligating compound having up to 20 atoms, other than hydrogen, and optionally L and X are bonded together;

X' is a divalent anionic ligand group having up to 60 atoms other than hydrogen;

x is 0, 1, 2, or 3;

t is a number from 0 to 2, and x' is 0 or 1.

3. A metal complex according to claim 1, corresponding to the formula:

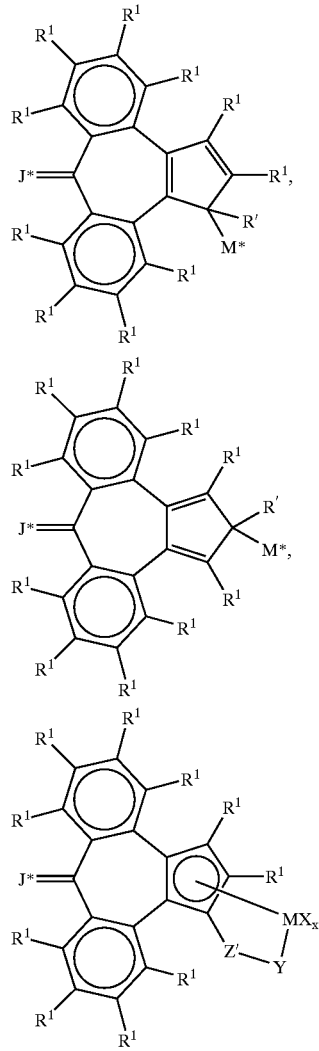

-continued

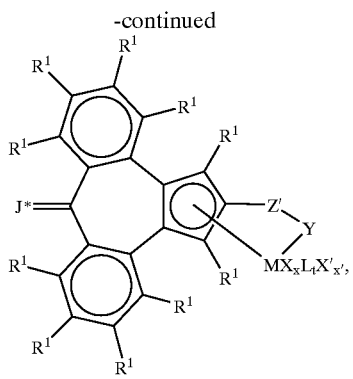

wherein,

M* is hydrogen, sodium, potassium or lithium;

M is titanium;

J* is methylene or difluoromethylene;

$R^1$ each occurrence is hydrogen or a hydrocarbyl, hydrocarbyloxy, dihydrocarbylamino, hydrocarbyleneamino, dihydrocarbylamino-substituted hydrocarbyl group, or hydrocarbyleneamino-substituted hydrocarbyl group of up to 20 atoms not counting hydrogen, and optionally two $R^1$ groups may be joined together;

Y is —O—, —S—, —$NR^5$—, —$PR^5$—; —$NR^5{}_2$, or —$PR^5{}_2$;

Z' is $SiR^6{}_2$, $CR^6{}_2$, $SiR^6{}_2SiR^6{}_2$, $CR^6{}_2CR^6{}_2$, $CR^6$=$CR^6$, $CR^6{}_2SiR^6{}_2$, $BR^6$, $BR^6L''$, or $GeR^6{}_2$;

$R^5$ each occurrence is independently hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$ each occurrence is independently hydrogen, or a member selected from hydrocarbyl, hydrocarbyloxy, silyl, halogenated alkyl, halogenated aryl, —$NR^5{}_2$, and combinations thereof, said $R^6$ having up to 20 non-hydrogen atoms, and optionally, two $R^6$ groups form a ring system;

X, L, L" and X' are as previously defined in claim 1;

x is 0, 1 or 2;

t is 0 or 1; and x' is 0 or 1;

and, when x is 2, x' is zero, M is in the +4 formal oxidation state (or M is in the +3 formal oxidation state if Y is —$NR^5{}_2$ or —$PR^5{}_2$), and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 atoms not counting hydrogen, when x is 0 and x' is 1, M is in the +4 formal oxidation state, and X' is a dianionic ligand selected from the group consisting of hydrocarbadiyl, oxyhydrocarbylene, and hydrocarbylenedioxy groups, said X group having up to 30 nonhydrogen atoms, when x is 1, and x' is 0, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when x and x' are both 0, t is 1, M is in the +2 formal oxidation state, and L is a neutral, conjugated or nonconjugated diene, optionally substituted with one or more hydrocarbyl groups, said L having up to 40 carbon atoms and being bound to M by means of delocalized π-electrons thereof.

4. A metal complex according to claim 1 selected from the group consisting of:

(8-methylene-1,8-dihydrodibenzo[e,h]azulen-1-yl)-N-(1,1-dimethylethyl)dimethylsilanamide titanium (II)1,4-diphenyl-3,3-butadiene, (8-methylene-1,8-dihydrodibenzo[e,h]azulen-1-yl)-N-(1,1-dimethylethyl)dimethylsilanamide titanium (II) 1,3-pentadiene, (8-methylene-1,8-dihydrodibenzo[e,h]azulen-1-yl)-N-(1,1-dimethylethyl)dimethylsilanamide titanium (III) 2-(N,N-dimethylamino)benzyl, (8-methylene-1,8-dihydrodibenzo[e,h]azulen-1-yl)-N-(1,1-dimethylethyl)dimethylsilanamide titanium (IV) dichloride, (8-methylene-1,8-dihydrodibenzo[e,h]azulen-1-yl)-N-(1,1-dimethylethyl)dimethylsilanamide titanium (IV) dimethyl, (8-methylene-1,8-dihydrodibenzo[e,h]azulen-1-yl)-N-(1,1-dimethylethyl)dimethylsilanamide titanium (IV) dibenzyl, (8-difluoromethylene-1,8-dihydrodibenzo[e,h]azulen-1-yl)-N-(1,1-dimethylethyl)dimethylsilanamide titanium (II) 1,4-diphenyl-1,3-butadiene, (8-difluoromethylene-1,8-dihydrodibenzo[e,h]azulen-1-yl)-N-(1,1-dimethylethyl)dimethylsilanamide titanium (II) 1,3-pentadiene, (8-difluoromethylene-1,8-dihydrodibenzo[e,h]azulen-1-yl)-N-(1,1-dimethylethyl)dimethylsilanamide titanium (III) 2-(N,N-dimethylamino)benzyl, (8-difluoromethylene-1,8-dihydrodibenzo[e,h]azulen-1-yl)-N-(1,1-dimethylethyl)dimethylsilanamide titanium (IV) dichloride, (8-difluoromethylene-1,8-dihydrodibenzo[e,h]azulen-1-yl)-N-(1,1-dimethylethyl)dimethylsilanamide titanium (IV) dimethyl, (8-difluoromethylene-1,8-dihydrodibenzo[e,h]azulen-1-yl)-N-(1,1-dimethylethyl)dimethylsilanamide titanium (IV) dibenzyl, (8-methylene-1,8-dihydrodibenzo[e,h]azulen-2-yl)-N-(1,1-dimethylethyl)dimethylsilanamide titanium (II) 1,4-diphenyl-1,3-butadiene, (8-methylene-1,8-dihydrodibenzo[e,h]azulen-2-yl)-N-(1,1-dimethylethyl)dimethylsilanamide titanium (II) 1,3-pentadiene, (8-methylene-1,8-dihydrodibenzo[e,h]azulen-2-yl)-N-(1,1-dimethylethyl)dimethylsilanamide titanium (III) 2-(N,N-dimethylamino)benzyl, (8-methylene-1,8-dihydrodibenzo[e,h]azulen-2-yl)-N-(1,1-dimethylethyl)dimethylsilanamide titanium (IV) dichloride, (8-methylene-1,8-dihydrodibenzo[e,h]azulen-2-yl)-N-(1,1-dimethylethyl)dimethylsilanamide titanium (IV) dimethyl, (8-methylene-1,8-dihydrodibenzo[e,h]azulen-2-yl)-N-(1,1-dimethylethyl)dimethylsilanamide titanium (IV) dibenzyl, (8-difluoromethylene-1,8-dihydrodibenzo[e,h]azulen-2-yl)-N-(1,1-dimethylethyl)dimethylsilanamide titanium (II) 1,4-diphenyl-1,3-butadiene, (8-difluoromethylene-1,8-dihydrodibenzo[e,h]azulen-2-yl)-N-(1,1-dimethylethyl)dimethylsilanamide titanium (II) 1,3-pentadiene, (8-difluoromethylene-1,8-dihydrodibenzo[e,h]azulen-2-yl)-N-(1,1-dimethylethyl)dimethylsilanamide titanium (III) 2-(N,N-dimethylamino)benzyl, (8-difluoromethylene-1,8-dihydrodibenzo[e,h]azulen-2-yl)-N-(1,1-dimethylethyl)dimethylsilanamide titanium (IV) dichloride, (8-difluoromethylene-1,8-dihydrodibenzo[e,h]azulen-2-yl)-N-(1,1-dimethylethyl)dimethylsilanamide titanium (IV) dimethyl, (8-difluoromethylene-1,8-dihydrodibenzo[e,h]azulen-2-yl)-N-(1,1-dimethylethyl)dimethylsilanamide titanium (IV) dibenzyl, and mixtures thereof.

5. An olefin polymerization process comprising contacting one or more olefin monomers under polymerization conditions with a catalyst composition comprising a metal complex according to any one of claims 1–4.

6. The process of claim 5 wherein the catalyst composition additionally comprises an activating cocatalyst.

7. The process of claim 5 conducted under solution, slurry or high pressure polymerization conditions.

8. The process of claim 5 conducted under slurry or gas phase polymerization conditions, wherein the catalyst additionally comprises an inert, particulated support.

9. The process of claim 6 wherein the activating cocatalyst is: trispentafluorophenylborane, methylditetradecylammonium tetrakis(pentafluorophenyl)borate, (pentafluorophenyl)ditetradecylammonium tetrakis(pentafluorophenyl)borate, dimethyltetradecylammonium tetrakis(pentafluorophenyl)borate, methyldihexadecylammonium tetrakis(pentafluorophenyl)borate, (pentafluorophenyl)dihexadecylammonium tetrakis(pentatluorophenyl)borate, dimethylhexadecylammonium tetrakis(pentafluorophenyl)-borate, methyldioctadecylammonium tetrakis(pentafluorophenyl)borate, (pentafluorophenyl)-dioctadecylammonium tetrakis(pentafluorophenyl)borate, dimethyloctadecylammonium tetrakis(pentafluorophenyl)borate, methylalumoxane, tri-isobutylaluminum modified methylalumoxane, or a mixture thereof.

* * * * *